(12) United States Patent
Kuzyk

(10) Patent No.: US 8,012,416 B2
(45) Date of Patent: Sep. 6, 2011

(54) THAWING BIOLOGICAL MATERIAL USING A SEALED LIQUID BLADDER

(75) Inventor: Roman Kuzyk, Trenton, NJ (US)

(73) Assignee: CytoTherm, L.P., Hamilton Sq., NJ (US)

( * ) Notice: Subject to any disclaimer, the term of this patent is extended or adjusted under 35 U.S.C. 154(b) by 979 days.

(21) Appl. No.: 11/461,161

(22) Filed: Jul. 31, 2006

(65) Prior Publication Data
US 2007/0127901 A1    Jun. 7, 2007

Related U.S. Application Data

(60) Provisional application No. 60/712,593, filed on Aug. 30, 2005.

(51) Int. Cl.
*A61L 2/00* (2006.01)
*A61B 18/14* (2006.01)
*A61F 7/08* (2006.01)

(52) U.S. Cl. ............................ 422/38; 604/114; 392/443

(58) Field of Classification Search .................. 604/114; 392/443; 422/38
See application file for complete search history.

(56) References Cited

U.S. PATENT DOCUMENTS

| | | | |
|---|---|---|---|
| 2,845,929 A | 8/1958 | Strumia | |
| 3,518,393 A | 6/1970 | Besseling | |
| 4,486,389 A | 12/1984 | Darnell et al. | |
| 4,539,005 A | 9/1985 | Greenblatt | |
| 4,549,670 A * | 10/1985 | Trendler | ........................ 422/104 |

(Continued)

FOREIGN PATENT DOCUMENTS
DE    3741051    6/1989
(Continued)

OTHER PUBLICATIONS

Thermogenesis, Plasma Thawers, "Simply the Best", 3 page advertisement.
(Continued)

*Primary Examiner* — Kevin C Joyner
(74) *Attorney, Agent, or Firm* — Donald R. Piper, Jr.; Dann Dorfman Herrell & Skillman, P.C.

(57) ABSTRACT

A method and apparatus are provided for thawing and heating biological material such as plasma, bone marrow or stem cells. The apparatus includes a housing containing a fluid-filled, sealed bladder for receiving a bag of the biological material. An agitator is provided which is operable to inflate an actuator pillow causing a support plate to compress the fluid-filled bladder, thereby promoting movement of the fluid within the bladder to agitate the biological material. A heater is provided which heats the fluid while contained in the bladder.

31 Claims, 4 Drawing Sheets

U.S. PATENT DOCUMENTS

| | | | | |
|---|---|---|---|---|
| 4,621,868 A * | 11/1986 | Slaats et al. | ............... | 297/344.19 |
| 4,808,159 A | 2/1989 | Wilson | | |
| 5,147,330 A | 9/1992 | Kogel | | |
| 5,243,833 A | 9/1993 | Coelho et al. | | |
| 5,282,264 A | 1/1994 | Reeves et al. | | |
| 5,403,279 A | 4/1995 | Inaba | | |
| 5,645,194 A | 7/1997 | Tyner | | |
| 5,733,263 A | 3/1998 | Wheatman | | |
| 5,743,878 A | 4/1998 | Ross et al. | | |
| 5,779,974 A | 7/1998 | Kuzyk | | |
| 6,007,773 A | 12/1999 | Kuzyk | | |
| 6,336,003 B1 | 1/2002 | Mitsunaga et al. | | |
| 6,748,164 B1 | 6/2004 | Kuzyk | | |
| 6,824,528 B1 | 11/2004 | Faiers et al. | | |
| 6,861,624 B1 * | 3/2005 | Pelster | ............... | 219/548 |
| 7,377,686 B2 * | 5/2008 | Hubbard | ............... | 366/208 |
| 2003/0082069 A1 * | 5/2003 | Kuzyk | ............... | 422/1 |

FOREIGN PATENT DOCUMENTS

| | | |
|---|---|---|
| EP | 0318924 B1 | 11/1988 |
| WO | WO 8807384 A1 * | 10/1988 |

OTHER PUBLICATIONS

Photo-Therm, Plasma Thawing System—Cyto-Therm III T, 2 page advertisement.

Photo-Therm, Plasma Thawing System—Cyto-therm CT S, 2 page advertisement.

Labor Technik Barkey, plasmatherm, 4 page advertisement.

Barkey, TCS Infusion Warming Concepts, phasmaterm, 3 page web advertisement.

Transmed®, "New: Thawing of Stem Cell Preparations with Sahara-TSC", 1 page advertisement.

* cited by examiner

THAWING BIOLOGICAL MATERIAL USING A SEALED LIQUID BLADDER

RELATED APPLICATIONS

This application claims priority to U.S. Provisional Application No. 60/712,593, filed Aug. 30, 2005, which is hereby incorporated herein by reference.

FIELD OF THE INVENTION

The present invention relates to an apparatus and method of quickly thawing biological materials, such as plasma, stem cells and bone marrow.

BACKGROUND OF THE INVENTION

Storing frozen biological material, such as plasma, and then thawing it for transfusions is common practice at health care facilities. Typically, bags of plasma or other such materials are frozen to preserve the plasma for subsequent use. For this purpose, plasma is usually stored frozen in a sealed prepackaged pouch or bag.

Before a frozen bag of plasma can be used for a transfusion, the frozen plasma must first be heated to a desired transfusable temperature. Conventionally, a wet bath has been used to warm the frozen plasma. To accomplish the thawing of the frozen plasma, a bag of the frozen plasma is placed directly into a liquid bath which has been preheated to a selected temperature necessary to thaw the frozen plasma. One of the problems with using a wet bath to effect plasma thawing is that contamination of the entire bath will occur if the plasma bag inadvertently leaks during the thawing process. Another problem is that contaminants in the bath may be transferred to the bag of plasma. Consequently, as an alternative to thawing the plasma by direct insertion into a wet bath, an overwrap bag has also been used to protect the bag of biological material and to isolate the bag in case of breakage. The disadvantage of overwrap bags is that they may not always be in convenient access or supply. In addition, the overwrap bags must also be sealed to prevent leakage. Furthermore, the overwrap bags become wet on the outside and must be wiped off with a towel. As a result, the towel and the overwrap bag become a potential breeding ground for bacteria.

As another matter, it is often desirable to thaw biological material rapidly, particularly in emergency situations. Rapid thawing of biological materials limits the amount of time thawed material sits in storage. Thawed plasma has a limited shelf life, and coagulant factors in thawed plasma can degrade in a relatively short period of time. If thawing time is relatively long, medical professionals will often compensate by removing extra frozen units of plasma out of cold storage in advance of an operation, so that a large volume of thawed plasma can be available by the time the operation begins. Of course, this results in wasted plasma if some of the extra units are not needed for the operation or transfusion. Rapid thawing allows medical professionals to have the proper amount of frozen biological materials on an as-needed basis, thereby reducing the potential for wasted materials. Accordingly, an apparatus or method for quickly thawing frozen biological materials in a dry environment is desirable.

SUMMARY OF THE INVENTION

In accordance with the present invention, an apparatus is provided for thawing biological material contained within a bag or other suitable container. More specifically, the thawing apparatus functions to agitate and heat the biological material to provide fast and sterile thawing.

In a particular aspect of the invention, an apparatus is provided for thawing frozen material. The apparatus comprises a housing for receiving the container of frozen material. A sealed, fluid-filled bladder is positioned within the housing to communicate with the container of frozen material. For example, the bladder may be configured to generally encapsulate or blanket the container of frozen material. In general, the bladder receives the container of frozen material within the housing. An example of such an arrangement is a bladder that surrounds the frozen material. An agitator is located within the housing and causes movement of the fluid-filled bladder to agitate the container of frozen material received by the bladder. In operation, the agitator may cause fluid located within the bladder to move or mix about, thereby functioning to also agitate the biological material. The agitator may include a deflatable and inflatable pillow positioned to move the bladder during inflation and deflation of the pillow. Finally, a heater is also positioned external of the bladder to heat the fluid in the fluid-filled bladder while the fluid is contained within the sealed bladder. In this manner, the fluid need not be removed from the bladder for heating and subsequent reintroduction back into the bladder. The heat provided by the heater functions to thaw the frozen material in the container.

More specifically, the apparatus may have an agitator which causes movement of both the bladder and the frozen material. The movement of the bladder may be effected by a pump that inflates and deflates an actuator pillow in communication or contact with the bladder. The pump may comprise several pump units which connect with separate pillow members of the actuator pillow. Each pillow member may be separately inflatable and deflatable to move different areas or portions of the bladder. To effect movement of the bladder, the bladder may be positioned on a bladder support that is moveable relative to the housing through the inflation and deflation of the actuator pillow. For example, inflation of the actuator pillow may cause at least a portion of the bladder support to move in a direction causing at least a portion of the fluid-filled bladder to compress. Deflation of the actuator pillow may allow the bladder support to move in a direction away from the bladder allowing at least a portion of the bladder to expand. The compression and decompression of at least portions of the bladder cause the fluid in the bladder to flow and thereby agitate and thaw the biological material. The bladder support may be provided as separate support plates, which optionally may be hinged together, thereby providing increased movement of the bladder upon inflation and deflation of the pillow.

To further enhance fluid flow, the bladder may be multi-chambered, comprising a first and a second section. The bladder may also be folded around the container of biological material to provide an upper bladder layer and a lower bladder layer with the container of biological material sandwiched therebetween. The bladder may be folded to sandwich the container to better surround the container of frozen material thereby providing, for example, an upper first chamber and a lower first chamber in a first section of the bladder and an upper second chamber and a lower second chamber in a second section of the bladder. The upper first chamber and upper second chamber may be connected by a one-way valve that permits fluid flow from the upper first chamber of the first section to the upper second chamber of the second section. Fluid may be free to flow from the upper second chamber to the lower second chamber across the fold of the bladder. Further, the lower first chamber and the lower second chamber may also be connected by a one-way valve that permits fluid flow from the lower second chamber of the second section to the lower first chamber of the first section. Fluid is also free to flow from the lower first chamber to the upper first chamber across the fold of the bladder. Inflation of a first pillow member of the inflatable and deflatable pillow may provide for the contraction of the first section within the bladder and expansion of the second section within the bladder. Inflation of a second pillow member of the inflatable and deflatable pillow may cause contraction of a second section within the bladder and the expansion of a first section within the bladder. Inflation of the pillow members by the pump provides for contraction of the chambers of the bladder in a controlled manner. This action of the agitator massages the bladder and helps to cause the fluid within the bladder to circulate through the sections and chambers of the bladder as controlled by the valves thereby providing for increased agitation and heating of the biological material.

The apparatus may have a controller operable to monitor and adjust the agitator and the heater. The apparatus may have a sensor which detects and adjusts the temperature of the fluid-filled bladder.

In a second aspect of the invention, a method is provided for thawing and heating biological materials in a container such as a bag. The container of frozen material is in communication with a sealed, fluid-filled bladder. The fluid-filled bladder is agitated to cause movement of the fluid-filled bladder and movement of the frozen material. Finally, the fluid within the sealed bladder is heated while the fluid is contained within the bladder by a heating element located external to the bladder.

More specifically, the bladder and biological material are agitated when the actuator pillow is inflated causing a bladder support to squeeze the first section of the bladder while permitting the second section of the bladder to expand. The actuator pillow may include separate pillow members either as separate sections of the actuator pillow or as entirely separate units. A pump unit inflates one pillow member causing the pillow member to expand and move the support to compress one section of the bladder while the second pillow member remains uninflated thereby permitting a second section of the bladder to expand. Conversely, when the second pillow member is inflated by the pump, the support contacts the second section of the bladder and causes it to compress while the first section of the bladder expands as the first pillow member contracts. While this process has been described in terms of compressing one section relative to a second section, compression is a relative term. In other words, if the second section is expanded while the first section remains constant, the first section, in essence, is still compressed in relative terms with respect to the second section.

BRIEF DESCRIPTION OF THE DRAWINGS

The foregoing summary as well as the following description will be better understood when read in conjunction with the figures in which.

DETAILED DESCRIPTION OF THE INVENTION

Figure 1:
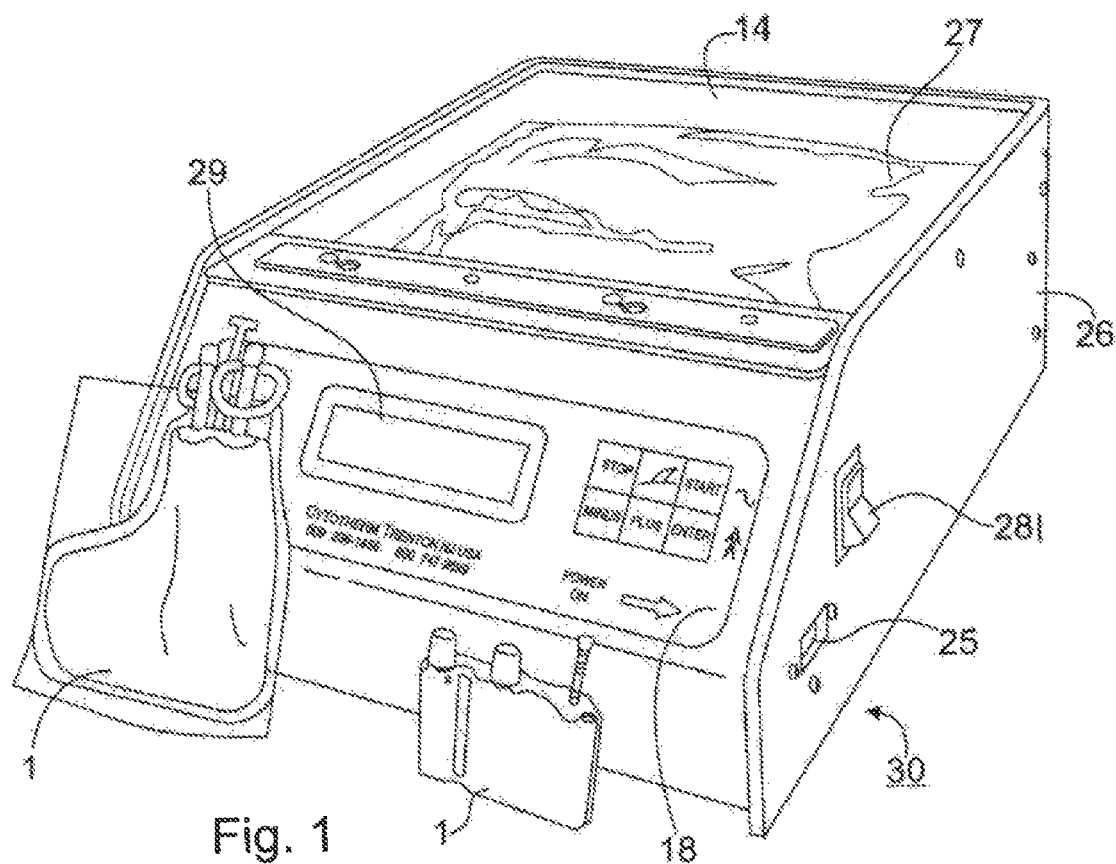
FIG. 1 is a perspective view of a thawing apparatus in accordance with the present invention.

Referring now to the Figures in general, wherein like reference numerals refer to the same components across the several views, there is shown an apparatus 30 for thawing and heating biological materials. The apparatus 30 is operable to thaw and heat biological materials 1 that are stored frozen or at low temperatures, including but not limited to plasma, bone marrow, and stem cells. For purposes of this description, the apparatus 30 will be described as it is used in connection with thawing and heating frozen bags of plasma.

Figure 2:
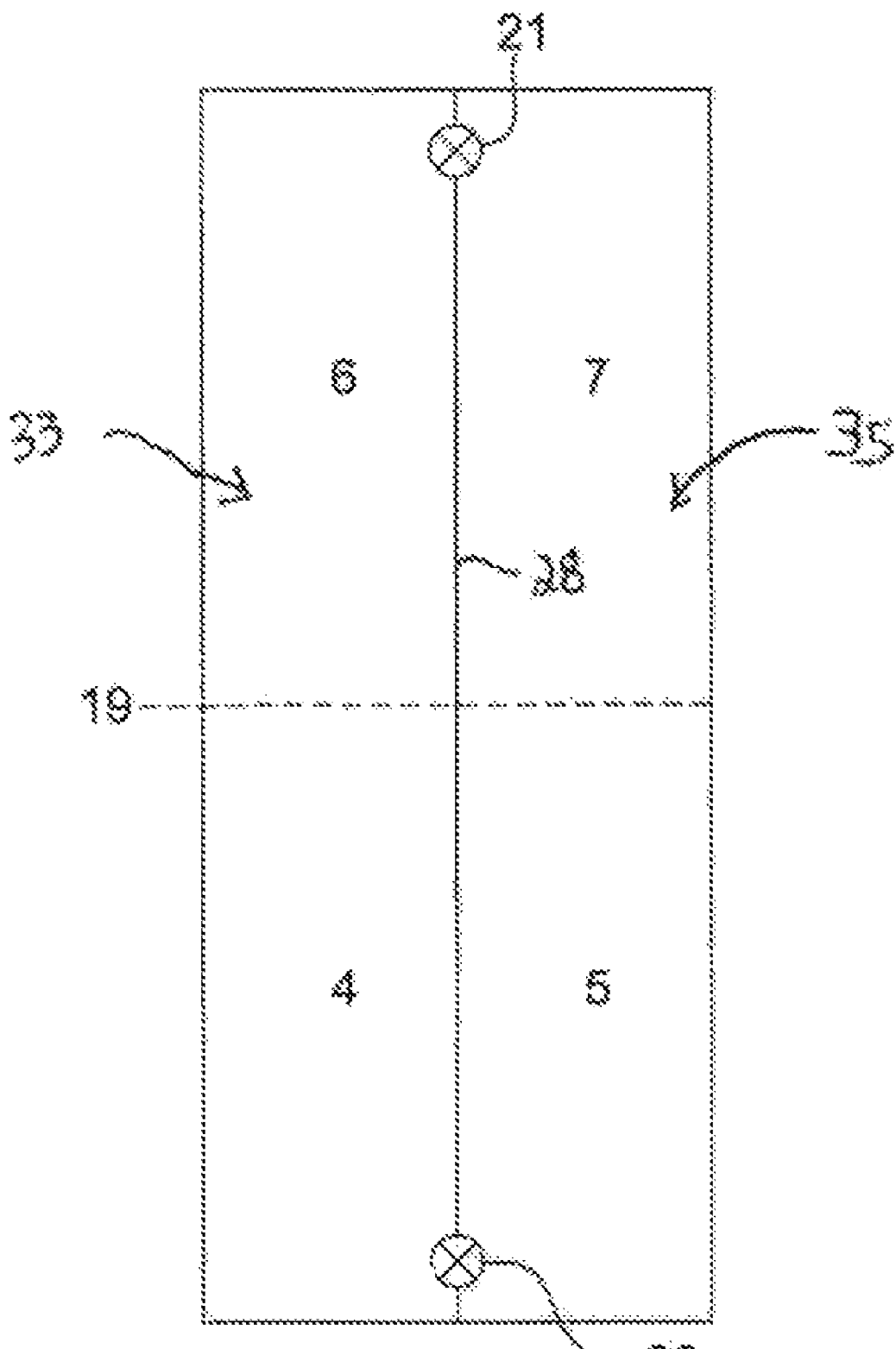
FIG. 2 is a top schematic view of a bladder used in the apparatus in FIG. 1.
Figure 3:
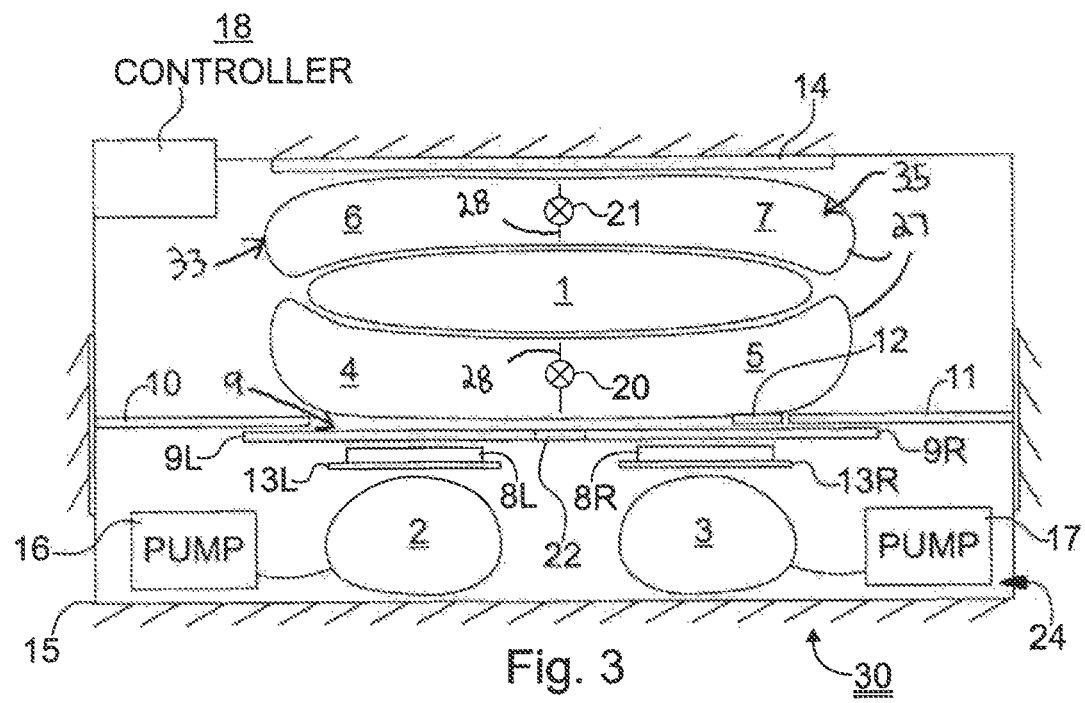
FIG. 3 is front schematic sectional view of the thawing apparatus in FIG. 1.
Figure 4:
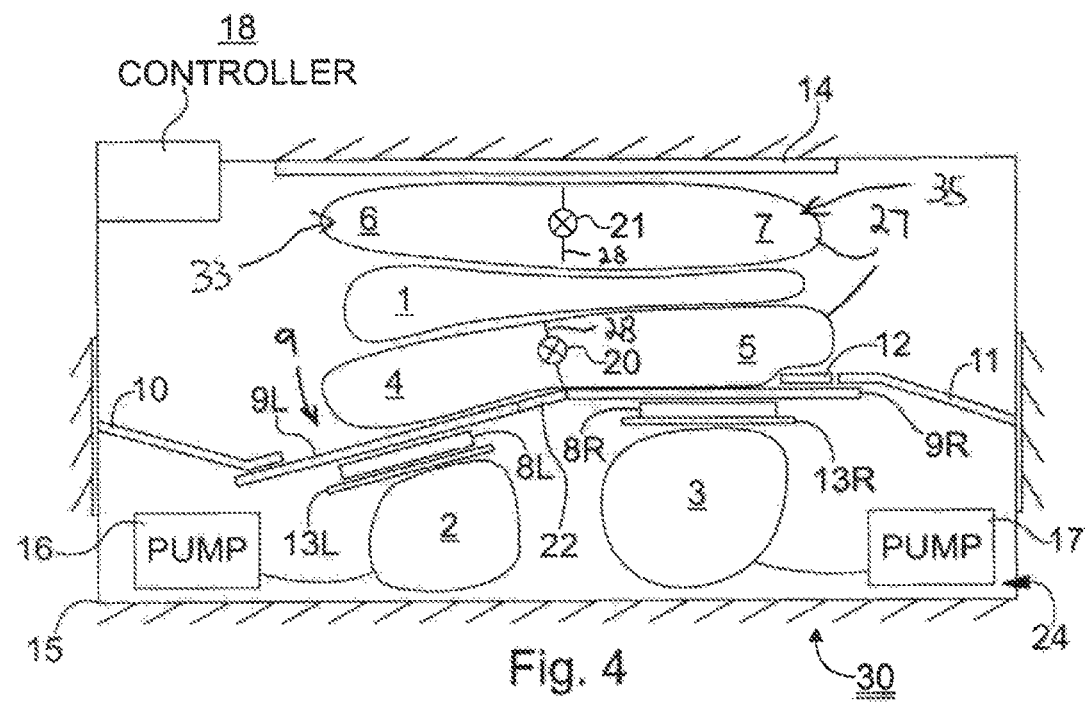
FIG. 4 is a front schematic sectional view of the thawing apparatus in FIG. 1 during operation with an agitator pillow in one position.
Figure 5:
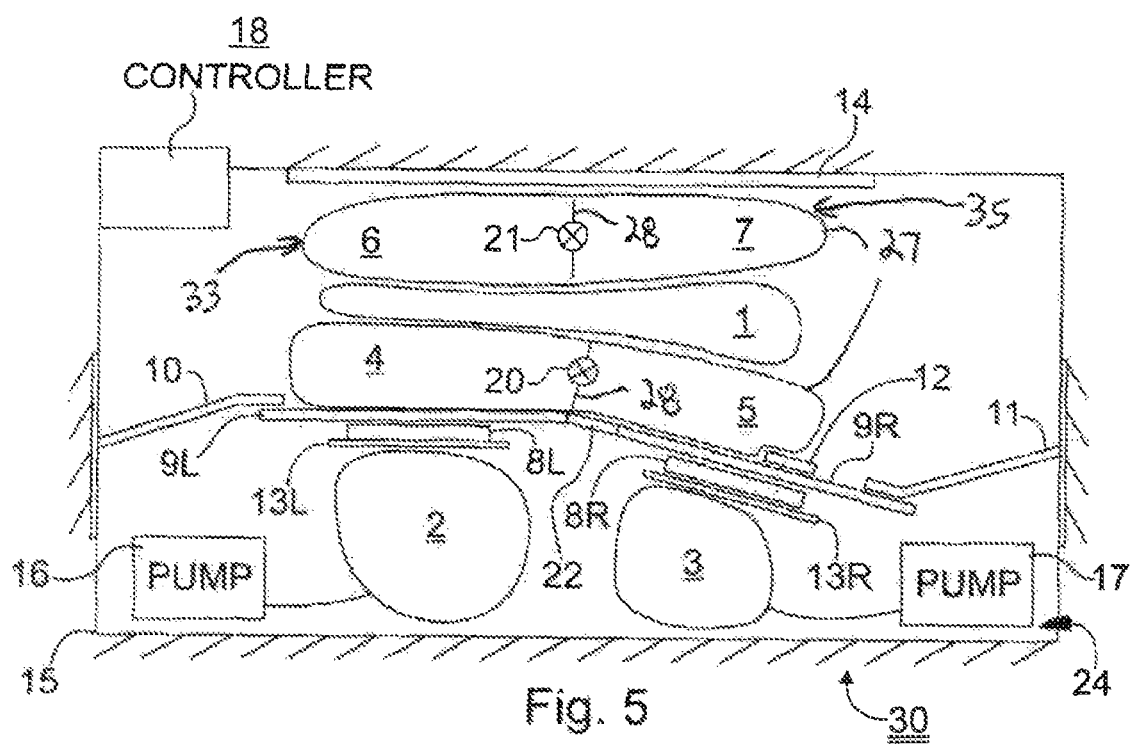
FIG. 5 is a front schematic sectional view of the thawing apparatus in FIG. 1 during operation with the agitator pillow in another position.

Referring now to FIGS. 1-5, the apparatus 30 includes a housing 26 and is configured to thaw a plasma bag in a closed hydraulic system that keeps the bag dry. By keeping the plasma bag dry, the sterility of the bag is maintained, and growth of bacteria is minimized. The housing 26 contains an agitator generally designated 24, in communication with a sealed, fluid-filled bladder 27, as shown in FIG. 3. The bladder 27 may be placed in contact with the plasma bag to be thawed. As shown in FIGS. 3-5, the fluid-filled bladder may be folded in half along fold line 19, as shown in FIG. 2, to enclose or encapsulate the bag of plasma 1 to increase or maximize the area of surface contact between the bladder 27 and the bag 1. More specifically, the bladder 27 may be folded generally in half to sandwich the bag of plasma between an upper and lower layer of the bladder. The bladder is filled with a suitable fluid to permit the bladder to conform to the outer shape of the bag 1. The fluid must also permit heat transfer from the bladder to the bag. The agitator 24 is operable to exert pressure through the fluid-filled bladder against the plasma bag. The agitator functions to move the fluid-filled bladder to effect movement of the bag. In operation the agitator functions to compress and decompress different portions of the bladder to effect a fluid flow within the bladder thereby resulting in movement of the bag. A heater 8, which may be provided by separate heater plates 8L and 8R, is operable to heat the fluid in the bladder to a desired temperature. The heated fluid in the bladder transfers heat to the biological material to aid in thawing the biological material.

A number of bladder configurations and agitator configurations may be used. For example, referring to FIG. 2, the bladder 27 is shown as a longitudinal container having a length-wise dividing web 28 that separates the bladder 27 into two separate elongated sections. As shown in FIGS. 3-5, the bladder may be folded in half approximately at the mid-section along fold line 19 so that one section 33 provides an upper chamber 6 and a lower chamber 4 and the other section 35 provides an upper chamber 7 and a lower chamber 5. Likewise, as shown in FIGS. 3-5 for example, the agitator 24 may include an actuator pillow having two pillow members 2, 3 connected to two pump units 16, 17. The pillow members 2 and 3 may be separate pillow units or they may be separate sections of a single pillow unit. Likewise, pump units 16 and 17 may be separate individual pumps or they may be different feed lines from a single pump. The agitator 24 is configured to pressurize and depressurize the pillow members 2, 3 intermittently or in a selected or preset sequence so that the pillow members expand and contract in different cycles. As the pillow members expand and contract, the bladder wall agitates the biological material to accelerate thawing.

Referring to FIG. 1, the apparatus 30 will now be described in greater detail. The housing 26 has a generally open top section. A door or lid 14 is pivotally mounted on the top side of the housing 26. The lid 14 is pivotal between an open position, which permits access to the interior of the housing 26, and a closed position, which limits access to the interior of the housing 26. Closing of the lid 14 provides a sealed, counteracting top surface against which the bladder and the bag are squeezed by the upward force of the agitator 24. Closing of the lid during use helps prevent heat loss to the atmosphere. Preferably, the lid 14 is formed of a heat-insulating transparent material, such as clear plastic, to permit viewing of the bag. In addition, the bladder 27 is preferably formed of a transparent material, such as transparent polyethylene. As such, the condition of the biological material bag 1 and the bladder 27 can be viewed through the lid 14 during operation of the apparatus 30. The apparatus can be operated by electric power, and is preferably configured to run on 120 VAC or 240 VAC. The housing 26 provides for an electrical port 25 so that the apparatus 30 can plug into an electrical outlet. A display 29 is located on the housing to display useful information to the user such as the rate or length of agitation as well as the temperature of the bladder or the bag. A controller 18 is provided to control the operation of the device. For example, the controller may control particular operational steps such as to stop agitation and heating of the material at selected times or temperatures or to increase or decrease the rate of agitation or the length of time the bag is to be agitated. A switch 281 is provided to power the apparatus by allowing the person operating the apparatus to turn the apparatus on and off.

Referring now to FIG. 3, the bladder 27 is supported within the housing on a bladder support 9 suspended within the housing. The bladder support 9 separates and seals the bladder 27 from the agitator 24 which is positioned within the housing below the bladder support 9. As shown in FIG. 3, the bladder 27 is configured to lay flat on the support 9 so that the bladder may be folded so as to wrap around the biological material bag 1.

Referring now to FIG. 2, the bladder 27 is depicted in an unfolded, laid-open configuration. The bladder 27 is made from a heat conductive material to facilitate heat transfer between the heater 8 and the fluid within the bladder and also between the fluid in the bladder and the biological material 1. The bladder should also be formed from a flexible or deformable material to enable the bladder to change shape. The bladder is sufficiently elongated so that the bottom chambers 4 and 5 of the bladder span the front to rear length of the housing while the top chambers 6 and 7 span the front to rear length of the covering lid 14. The bladder is sealed along the periphery to seal the fluid within the bladder. As shown in FIG. 2, the dividing wall 28 extends the length of the bladder to separate the bladder into two length-wise sections. In use, the bladder folds along line 19 so that the top and bottom chambers of the bladder may be unfolded open and folded closed as the lid 14 is opened and closed. In such a configuration, the respective upper chambers 6 and 7, as shown in FIG. 2, communicate with the respective bottom chambers 4 and 5 to permit fluid flow therebetween through the fold line 19. Alternatively, the bladder may comprise four separate chambers with each chamber being connected other chambers by tubing. In another embodiment, the bladder may comprise two chambers connected by tubing or valves and may lay flat on the support and not fold around the frozen material.

The bladder 27 is filled with fluid and is made of flexible material which is able to conduct heat. It is advantageous to fill the bag with fluid because the temperature uniformity of fluid aids in rapidly thawing the bag of plasma. Further, the fluid allows the bladder to change and conform its shape around the bag of plasma thereby promoting uniform heat transfer from the fluid in the bladder to the biological material. Use of a sealed bladder is a safe and sterile way to thaw biological materials. Contaminants are unable to enter the fluid since the bladder 27 is sealed.

Another advantage of sealing the bladder 27 with fluid contained therein is that much less fluid is used in a sealed bladder than in a system that employs a separate reservoir for circulating fluid in and out of the bladder. Furthermore, the sealed bladder prevents spilling and sloshing of fluid in and out of the bladder which may sometimes occur when using a reservoir. By using a sealed bladder as little as one liter of fluid may be used to fill the bladder, whereas traditional systems which employ reservoirs might use many more liters of fluid to fill the reservoir and circulate through the bladder.

More specifically, as shown in FIGS. 2, 3, 4 and 5, the bladder 27 may contain multiple sections and chambers. The first section 33 is sealed from the second section 35 by dividing web 28. When in use, the first section has an upper chamber 6 and a lower chamber 4, and the second section has an upper chamber 7 and a lower chamber 5. The upper chamber 6 is separated from the lower chamber 4 in the first section by the fold 19 in the bladder. Likewise, the upper chamber 7 is separated from the lower chamber 5 in the second section by the fold 19 in the bladder. The bag is not sealed at fold line 19 in order to provide for flow of fluid between the lower and upper portions of the chambers in each section. The upper chambers 6 and 7 are connected by a check valve 21. The lower chambers 4 and 5 are connected by a check valve 20.

The multiple sections and valves in the bladder 27 permit fluid to better circulate through the bladder 27 in a controlled manner. The fluid circulates in one direction through the chambers thereby providing a more efficient flow of heated fluid throughout the bladder and thereby speeds thawing of biological materials 1. More specifically, referring to FIGS. 3, 4 and 5, fluid flows from the upper left chamber 6 through the check valve 21 into the upper right chamber 7. The check valve 21 prevents a back flow of fluid from the upper right chamber 7 into the upper left chamber 6 as depicted in FIGS. 3-5. Then, the fluid flows down through the second section 35 from upper chamber 7 across the fold 19 in the bladder into lower right chamber 5. Fluid then flows from the lower right chamber 5 through the check valve 20 into the lower left chamber 4. Again, check valve 20 prevents back flow through the valve. Next, the fluid flows up across the fold line 19 into the upper chamber 6 of the first section. Check valves 20 and 21 permit fluid to flow in only one direction. Accordingly, since fluid is unable to flow back through the valve 21 from chamber 7 into chamber 6, or back through valve 20 from chamber 4 into chamber 5, fluid flows more efficiently through the bladder.

Fluid located in the bottom chambers 4 and 5 of the bladder is heated by the heater 8. As the heated fluid circulates through the bladder, the heated fluid can flow to the upper chambers 6 and 7 of the bladder to heat the upper surface of the bag 1 to thereby promote more even heating of the biological material 1 and to increase the rate of thawing of the biological material 1.

Operation of the agitator 24 will now be considered in greater detail. The agitator 24 functions to compress and decompress the bladder to circulate the heating fluid though the bladder. The agitator is generally located in the bottom section of the apparatus as shown in FIGS. 3, 4, and 5. The agitator 24 comprises a pump which may have pump units 16 and 17 and an actuator pillow which may have at least two pillow members 2 and 3. The agitator 24 is sealed in a separate compartment within the housing below the bladder by the bladder support 9. The bladder support 9 includes support plates 9L and 9R and web-like supports 10 and 11 that interconnect the support plates in a sealed manner with the internal walls of the housing. The bladder support 9 spans the width and length of the housing to separate the bladder from the agitator. The bladder rests on the support plates 9L and 9R which are suspended by the web-like supports 10 and 11 in such a manner to permit movement of the support plates by the pillows 2 and 3. Located below the bladder support 9 is a heater 8 that functions to heat heating elements 8L and 8R positioned to respectively communicate with support plates 9L and 9R. As shown in FIGS. 3-5, the support plates 9L and 9R respectively rest upon the heating elements 8L and 8R to ensure good thermal conduction from the heating elements through the support plates and into the bladder. Preferably, the web-like supports 10 and 11 provide proper insulation to minimize heat loss through the web-like supports 10 and 11 and to maximize heat conduction through the support plates and into the bladder. To minimize heat transfer to the pillow members 2 and 3, insulation in the form of insulation pads 13L and 13R are respectively positioned between the heating elements 8L and 8R and the respective pillow members 2 and 3 disposed respectively beneath the heating elements 8L and 8R for respective support plates 9L and 9R. The pillow members 2, 3 are connected to a pump which may include separate pump units 16, 17 for each pillow. The pillow members 2, 3 and the pump units 16, 17 may rest on the base 15 of the apparatus 30 within the housing.

Turning to the web-like supports 10 and 11, these supports connect the support plates 9L and 9R with the front, back and sides of the housing 26. The web-like supports 10 and 11 preferably are made of a silicone elastic material which allow the support 9 to have free range of motion. The web-like supports 10 and 11 separate the bladder and the agitator. In this way, the web-like supports hold any fluid that may leak from a broken bag of biological material or a broken bladder, thereby providing easy clean up of the apparatus 30.

The support plates 9L and 9R are preferably made of a heat conductive metal to provide for increased heat conductance from the heater to the bladder 27. The suspended support plates 9L and 9R function to support the bladder and to conduct heat from the heating elements 8L and 8R to the bladder. As shown in FIGS. 3-5, the fluid-filled bladder may rest upon the support plates 9L and 9R so that support plate 9L moves a particular portion of the bladder, such as the first section of the bladder, and support plate 9R moves another portion of the bladder, such as the second section of the bladder. In operation the agitator 24 moves the support plates 9L and 9R to agitate the bladder to thereby move the container of frozen material. In the arrangement shown in FIGS. 3-5, one support plate 9L is located on the left side of the apparatus, and another support plate 9R is located on the right side of the apparatus. The support plates 9L and 9R may be joined together in a fixed manner so that both plates move in unison. Alternatively, the support plates 9L and 9R may be separated so that one support plate 9L moves separately from the other support plate 9R. The middle of the bladder support 9 may contain a hinge 22 for joining the support plates 9L and 9R together while enabling each support plate to move independently of the other. The hinge 22 provides for increased movement of the bladder in response to the inflation and deflation of the pillow members 2 and 3. This increased movement further aids in circulation of fluid through the bladder.

The heater 8 comprises at least two heater plates 8L and 8R. Each heater plate 8L and 8R is located under a respective metal support plate 9L and 9R, and each heater plate 8L and 8R may directly contact the underside of the respective support plates 9L and 9R. Each heater plate 8L and 8R is free to move with its respective support plate 9L and 9R so that the heater does not restrict the range of motion of the support plates 9L and 9R. The apparatus 30 also comprises an insulator 13. The insulator may include separate insulator pads 13L and 13R secured to the underside of the respective heating elements 8L and SR to ensure a free range of motion. As shown in FIGS. 3-5, each insulator pad, 13L and 13R, is located between the respective heating element 8L and 8R and the pillow member 2 and 3. For example, on the left side of FIG. 3, insulator 13L is located between heater element 8L and pillow member 2. On the right side, insulator 13R is located between heater 8R and pillow 3. The insulating material protects the actuator pillows from the heater elements and minimizes heat loss.

At least one pump is provided for connection to the actuator pillow. As shown, for example, in FIG. 3, pump unit 16 connects to pillow member 2 and pump unit 17 connects to pillow member 3. Optionally, a single pump can connect to both pillow members. Each pump unit operates to inflate or deflate the respective pillow member. While pillow members may be provided for rocking the support plate 9, any other type of actuator may be used in different arrangements or configurations.

Operation of the device will now be considered with reference to FIGS. 3-5. FIG. 3 shows the apparatus at rest. The bladder is resting on the support plates 9L and 9R. The pillow members 2, 3 are not inflated and do not compress the bladder.

FIG. 4 illustrates a first part of the circulation cycle of the apparatus. The pump unit 17 has expanded pillow member 3, thereby pushing the heater 8R and support plate 9R upward towards the bladder. Section 35 of the bladder is thereby compressed. More specifically, two chambers of the bladder, lower chamber 5 and upper chamber 7 of section 35, are compressed by the support plate 9R and exert pressure on the right side of the bag of biological material 1. The web-like support 11 flexes upward with the support plate 9R. At the same time, pillow member 2 contracts, and the heater element 8L and support plate 9L move downward away from the bladder. Web-like support 10 stretches in connection with plate 9L to extend away from the bladder. The left section 33 of the bladder is therefore able to expand. Fluid within the bladder flows from upper chamber 7 and flows across fold 19 into lower chamber 5. Fluid within the bladder also flows from lower chamber 5, through valve 20 and enters lower chamber 4. The squeezing of the right side of the bag of biological fluid by the bladder portions 5 and 7 massages the frozen biological material. The compression of fluid out of chambers 5 and 7 thoroughly mixes the fluid thereby maintaining an even temperature of the fluid within the bladder.

FIG. 5 illustrates a second part of the circulation cycle of the apparatus 30. Pump unit 16 expands pillow member 2 causing the heater element 8L and support plate 9L to move upwards towards the bladder. The web-like support 10 stretches upward with the support plate 9L thereby keeping the agitator 24 sealed from the bladder 27 and the bag of biological material 1 in the event of a leak. Two chambers of the bladder, lower chamber 4 and upper chamber 6 of section 33, are compressed by the support plate 9L thereby applying pressure to the left side of the bag of biological material. Simultaneously, pillow member 3 is compressed thereby allowing the heater SR and the support plate 9R to move downward away from the bladder. Web-like support 11 moves in conjunction with plate 9R away from the bladder. The right section 35 of the bladder expands thereby causing upper chamber 7 and lower chamber 5 to expand. The movement of the bladder causes the fluid within the bladder to circulate from lower chamber 4 across the fold line 19 into upper chamber 6 and then from upper chamber 6 through check valve 21 into upper chamber 7. Also, fluid flows from upper chamber 7 across fold 19 into lower chamber 5.

This cycle illustrated in FIG. 4 followed by FIG. 5 is repeated by the apparatus 30 until the biological material is thawed. The alternating expansion and contraction of the first and second bladder sections 33 and 35 cause the bladder wall to move and massage the bag of biological material 1. Movement of the bladder causes the fluid heated in the bottom layer of the bladder to mix and circulate with fluid in the upper layer of the bladder and agitates the biological material 1 to assist in thawing. In operation, the thawing process can be observed by looking through the transparent lid 14 and transparent bladder. The agitator may operate until a preset time or a selected time entered at the control panel 18 expires or until sensor 12 detects a preset temperature or a selected temperature at the bladder. For this purpose, the sensor 12 is located between the bladder 27 and the agitator 24 as shown in FIGS. 3-5. The sensor 12 monitors and maintains the temperature of fluid in the reservoir to a suitable temperature for thawing biological material. For example, a programmable thermostat may be provided to regulate the temperature of fluid to a preset temperature. The thermostat may be set to 37° C. (98.6° F.) to heat a quantity of plasma to a temperature compatible with a patient's body temperature. Likewise, the thermostat may be set to any necessary temperature above or below body temperature. The thermostat may be wired to the heater and the controller to switch the heater on when the fluid in the bladder falls below a desired temperature, or to switch the heater off when the fluid temperature exceeds the desired temperature. A digital or LCD display 29 may be provided to display operating conditions in the apparatus, including elapsed heating time, temperature in the fluid reservoir, or the presence of a leak in the bladder. A variety of other controls and sensors may be used with the apparatus 30.

In an alternative mode of operation, the agitator 24 may shut off as a selected time expires. If the biological material still appears partially frozen, the agitator and heater may be restarted to thaw the plasma for an additional amount of time. The thawing cycle may be terminated manually before the programmed time expires by pressing a stop button on the control panel 18. Once the pump units 16, 17 are stopped, the pillow members 2, 3 return to the resting state and pressure is released from the biological material bags 1. In addition, if the heater 8 is running, the heater is shut off. In an alternative mode of operation, the apparatus. may operate in response to temperature settings or in response to both temperature and time settings.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. An apparatus for thawing frozen material in a container comprising:
    A) a housing for receiving the container of frozen material;
    B) a sealed fluid-filled bladder contained within the housing for thermally communicating with the container of frozen material;
    C) an agitator in the housing for causing movement of the fluid-filled bladder and the container of frozen material communicating with the bladder, wherein the agitator comprises an inflatable and deflatable actuator pillow communicating with the sealed bladder to effect movement of the bladder to thereby move the container of frozen material in communication with the bladder; and
    D) a heater positioned within the housing external of the bladder to heat the fluid in the fluid-filled bladder while the fluid is contained within the sealed bladder to thaw the frozen material in the container.

2. The apparatus of claim 1, wherein the actuator pillow includes at least two pillow members that are inflatable and deflatable to effect movement of different areas of the bladder.

3. The apparatus of claim 2, wherein the pillow members are inflatable and deflatable in a selected sequence relative to one another to effect sequential movement of different areas of the bladder.

4. The apparatus of claim 3, wherein the pillow members are inflated and deflated to effect a cyclical type motion of the container of frozen material in communication with the bladder.

5. The apparatus of claim 2, comprising a controller operable to monitor and adjust the movement of the actuator pillow.

6. The apparatus of claim 2, wherein the pillow members are disposed at different positions beneath the bladder.

7. The apparatus of claim 2, wherein the pillow members are separate from one another and are separately inflatable and deflatable relative to one another.

8. The apparatus of claim 2, wherein the agitator includes a pump and wherein the bladder has multiple chambers and wherein further expansion of a first one of the pillow members by the pump causes contraction of a first one of the chambers within the bladder and expansion of a second one of the chambers within the bladder.

9. The apparatus of claim 8, wherein expansion of a second one of the pillow members by the pump causes contraction of a second one of the chambers within the bladder and expansion of a first one of the chambers within the bladder.

10. The apparatus of claim 1, wherein the agitator includes a pump connected with the actuator pillow to alternatively inflate and deflate the actuator pillow.

11. The apparatus of claim 10, wherein the actuator pillow includes at least two separate pillow members and wherein the pump includes a separate pump unit for each pillow member.

12. The apparatus of claim 1, comprising an insulator positioned between the heater and the actuator pillow.

13. The apparatus of claim 1, comprising a controller operable to monitor and adjust the heater to control the temperature of the fluid in the bladder.

14. The apparatus of claim 13, comprising a sensor to detect the temperature of the fluid in the bladder and the biological material wherein said heater is responsive to the sensor to adjust the temperature.

15. The apparatus of claim 14, wherein the sensor cooperates with the agitator so that the sensor ceases operation of the agitator at selected, predetermined temperatures.

16. An apparatus for thawing frozen material in a container comprising:
    A) a housing for receiving the container of frozen material;
    B) a sealed fluid-filled bladder contained within the housing for thermally communicating with the container of frozen material;
    C) an agitator in the housing for causing movement of the fluid-filled bladder and the container of frozen material communicating with the bladder; and
    D) a heater positioned within the housing external of the bladder to heat the fluid in the fluid-filled bladder while the fluid is contained within the sealed bladder to thaw the frozen material in the container;

wherein the bladder includes a first section and a second section, and wherein said first and second sections are connected by at least two valves, one valve permitting fluid flow from the first section to the second section and the other valve permitting fluid flow from the second section to the first section.

17. The apparatus of claim 16, wherein the agitator is in communication with the first and second sections and operates to compress the first section relative to the second section to cause fluid to flow from the first section through the valve permitting fluid to flow into the second section.

18. The apparatus of claim 17, wherein the agitator functions to thereafter compress the second section relative to the first section to cause fluid to flow from the second section through the other valve and back into the first section.

19. An apparatus for thawing frozen material in a container comprising:
A) a housing for receiving the container of frozen material;
B) a sealed fluid-filled bladder contained within the housing for thermally communicating with the container of frozen material;
C) an agitator in the housing for causing movement of the fluid-filled bladder and the container of frozen material communicating with the bladder; and
D) a heater positioned within the housing external of the bladder to heat the fluid in the fluid-filled bladder while the fluid is contained within the sealed bladder to thaw the frozen material in the container;
wherein the fluid-filled bladder includes four chambers for the circulation of the fluid therethrough.

20. An apparatus for thawing frozen material in a container comprising:
A) a housing for receiving the container of frozen material;
B) a sealed fluid-filled bladder contained within the housing for thermally communicating with the container of frozen material;
C) an agitator in the housing for causing movement of the fluid-filled bladder and the container of frozen material communicating with the bladder; and
D) a heater positioned within the housing external of the bladder to heat the fluid in the fluid-filled bladder while the fluid is contained within the sealed bladder to thaw the frozen material in the container;
wherein the bladder has multiple chambers and wherein the agitator is activated to cause contraction of one of the chambers of the bladder, thereby effecting movement of fluid from the contracted chamber through at least one check valve into at least one other chamber of the bladder.

21. The apparatus of claim 1, 16, 19, or 20, comprising a bladder support for supporting the bladder within the housing.

22. The apparatus of claim 21, wherein the agitator moves the bladder support to agitate the bladder and move the container of frozen material.

23. The apparatus of claim 22, wherein the bladder support includes a web-like support which connects with the housing and seals the agitator from the bladder.

24. The apparatus of claim 21, wherein the bladder support comprises at least two separately movable support plates.

25. The apparatus of claim 24, wherein the bladder support includes a hinge and wherein the support plates are interconnected with the hinge.

26. The apparatus of claim 21, wherein the bladder support includes a hinge to effect movement of the bladder and the container of frozen material.

27. The apparatus of claim 26, wherein the hinge comprises an elastic material.

28. The apparatus of claim 1, 19, or 20, wherein the bladder has two chambers located above the container of the frozen material and two chambers located below the container of the frozen material.

29. The apparatus of claim 28, wherein the agitator is activated to cause contraction of a first one of the upper and a first one of the lower chambers of the bladder, thereby effecting movement of fluid from the contracted first one of the upper chambers into the contracted first one of the lower chambers, and effecting fluid flow from the contracted first one of the lower chambers through a check valve into a second one of the lower chambers of the bladder and then into a second one of the upper chambers of the bladder.

30. The apparatus of claim 29, wherein the agitator is activated to cause contraction of such second one of the upper chamber and the second one of the lower chamber of the bladder, thereby effecting movement of fluid from such second one of the lower chambers into such second one of the upper chambers, and effecting fluid flow from such second one of the upper chambers through a check valve and back into the first one of the upper chambers of the bladder and into the first one of the lower chambers of the bladder.

31. The apparatus of claim 28, wherein an upper chamber and a lower chamber of the bladder are connected by a fold in the bladder.

* * * * *